United States Patent
Höfle et al.

(10) Patent No.: US 7,172,607 B2
(45) Date of Patent: Feb. 6, 2007

(54) DEVICE FOR GENERATING AN ARTIFICIAL CONSTRICTION IN THE GASTROINTESTINAL TRACT

(75) Inventors: Siegfried Höfle, Feldkirch (AT); Walter Egle, Koblach (AT)

(73) Assignee: Ami Agency for Medical Innovations GmbH, Gotzis (AT)

( * ) Notice: Subject to any disclaimer, the term of this patent is extended or adjusted under 35 U.S.C. 154(b) by 424 days.

(21) Appl. No.: 10/638,807

(22) Filed: Aug. 12, 2003

(65) Prior Publication Data
US 2004/0158272 A1    Aug. 12, 2004

(30) Foreign Application Priority Data

Aug. 16, 2002  (EP)  .................... 02018449
Jan. 11, 2003  (EP)  .................... 03000473

(51) Int. Cl.
*A61B 17/08* (2006.01)
(52) U.S. Cl. ...................... 606/151; 606/157
(58) Field of Classification Search ............... 606/157, 606/151; 600/31, 37, 587, 561; 604/103.07, 604/909; 623/23.65
See application file for complete search history.

(56) References Cited

U.S. PATENT DOCUMENTS

| | | | |
|---|---|---|---|
| 4,911,176 A * | 3/1990 | Timm et al. | 600/587 |
| 5,152,770 A | 10/1992 | Bengmark et al. | |
| 5,207,694 A * | 5/1993 | Broome | 606/148 |
| 5,601,604 A * | 2/1997 | Vincent | 606/216 |
| 6,511,490 B2 * | 1/2003 | Robert | 606/151 |
| 6,676,674 B1 * | 1/2004 | Dudai | 606/151 |
| 6,916,326 B2 * | 7/2005 | Benchetrit | 606/151 |
| 6,966,875 B1 * | 11/2005 | Longobardi | 600/31 |

FOREIGN PATENT DOCUMENTS

| | | |
|---|---|---|
| EP | 1 205 148 | 5/2002 |
| FR | 2 799 118 | 4/2001 |
| FR | 2 802 406 | 6/2001 |

\* cited by examiner

*Primary Examiner*—(Jackie) Tan-Uyen Ho
*Assistant Examiner*—Natalie Pous
(74) *Attorney, Agent, or Firm*—Wenderoth, Lind & Ponack, L.L.P.

(57) ABSTRACT

A device for generating an artificial constriction in a gastrointestinal tract includes a band, which can be placed annularly about a particular portion of the gastrointestinal tract, having a fillable hollow volume, and a closure device for connecting end regions of the band placed annularly about the portion of the gastrointestinal tract. The closure device is a safety closure, which, at a tear-off tension exceeding a limit value, opens free of destruction, and which can be closed again. This limit value of the tear-off tension is in the range between 20 and 60 N, and preferably between 30 and 50 N.

18 Claims, 3 Drawing Sheets

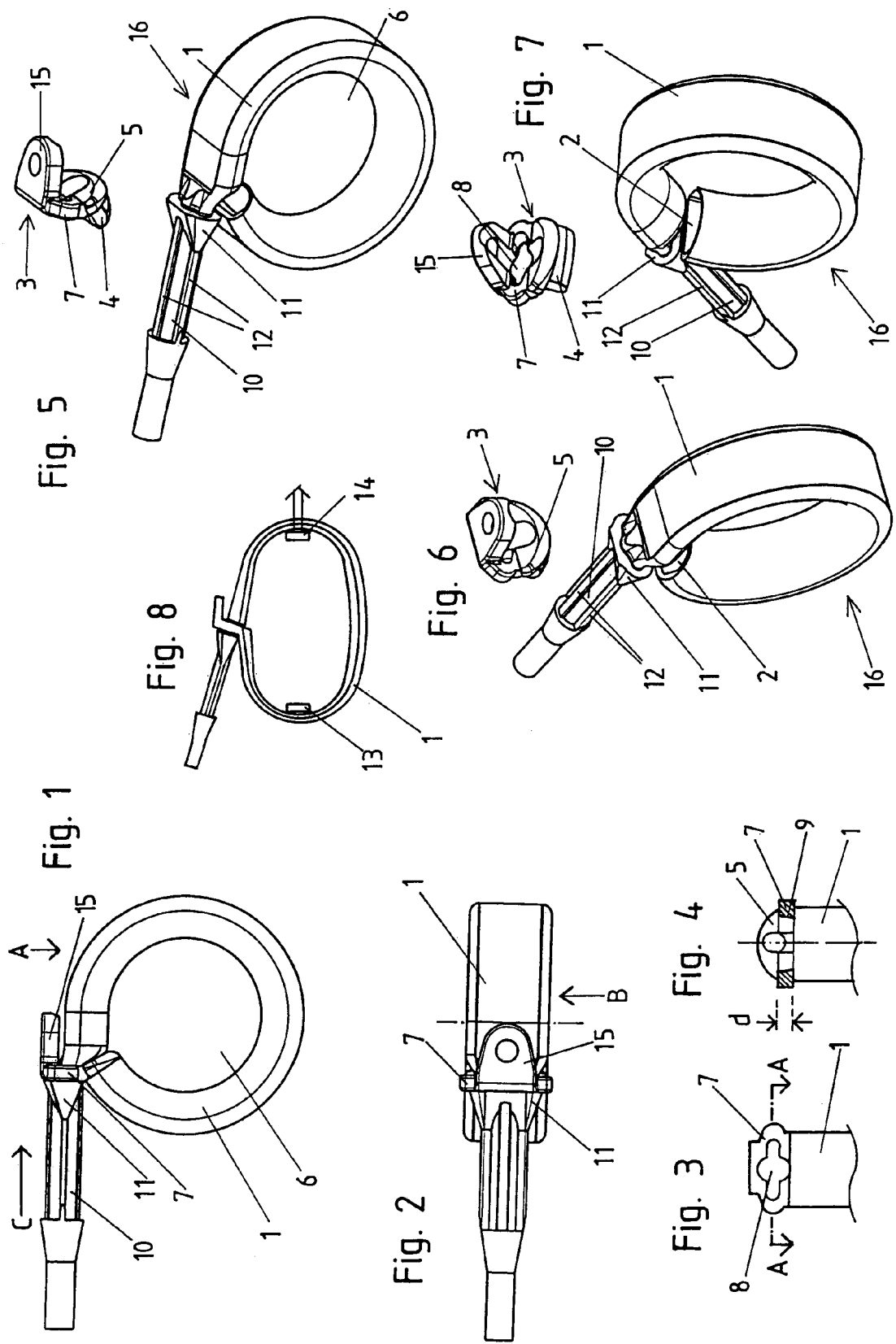

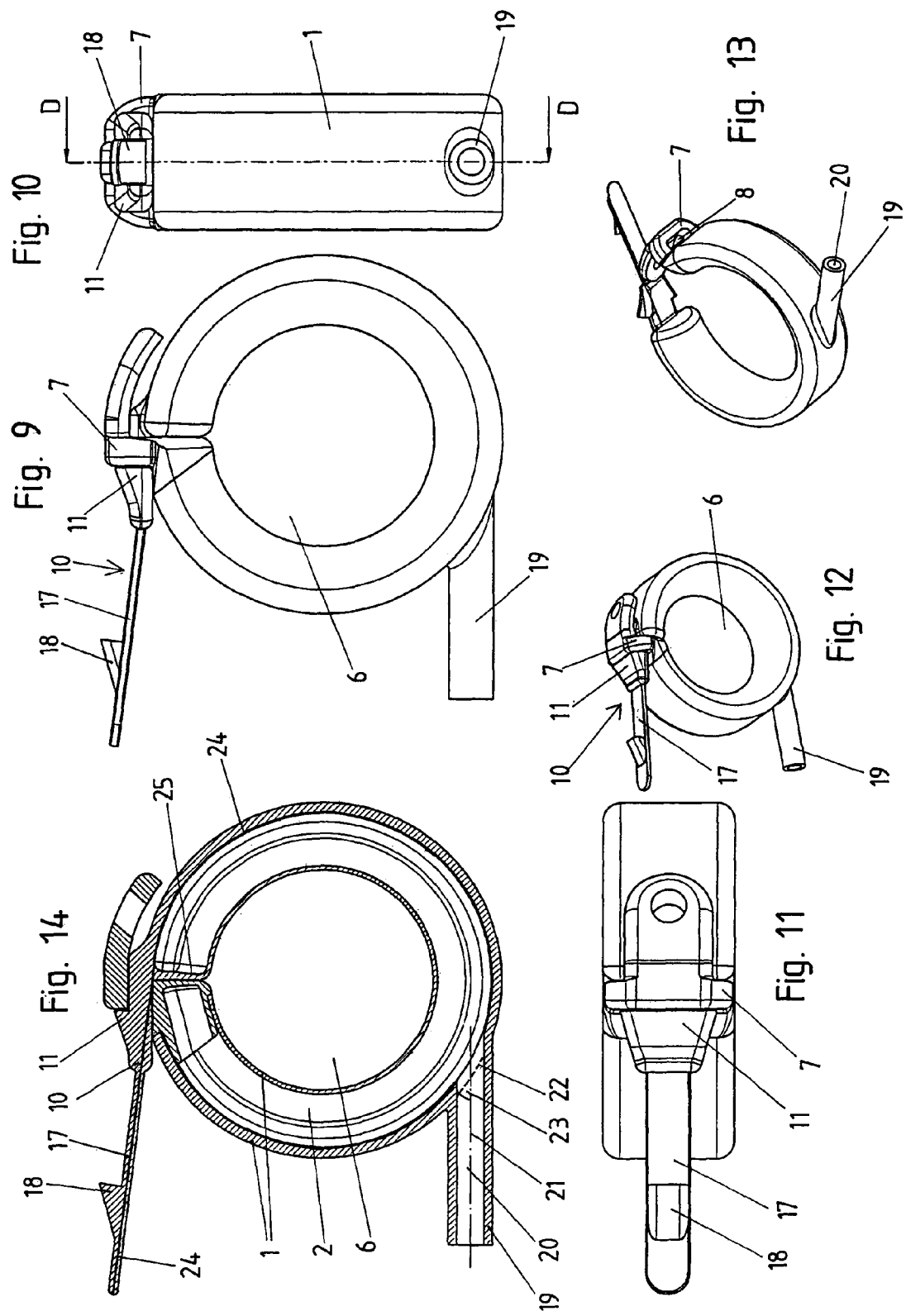

DEVICE FOR GENERATING AN ARTIFICIAL CONSTRICTION IN THE GASTROINTESTINAL TRACT

BACKGROUND OF THE INVENTION

1. Field of the Invention

The invention relates to a device for generating an artificial constriction in the gastrointestinal tract with a band which can be placed annularly about the particular portion of the gastrointestinal tract. The band comprises a fillable hollow volume, and a closure device for connecting the end regions of the band placed annularly about the portion of the gastrointestinal tract.

2. Description of the Related Art

Such a device is disclosed, for example, in the form of a stomach band in EP 1 205 148 A1. The device comprises a band which can be placed about the inlet to the stomach, which is developed with an inner opening extending longitudinally. To irreversibly close the band placed annularly about the stomach inlet, it comprises a closure with a first closure part disposed on one end of the band and an insertion opening and a second closure part disposed on the other end of the band, which can be introduced through the insertion opening and can be snapped facing it.

In a further prior known stomach band, straps are disposed on both ends of the band. In one strap, a lead-through opening is provided through which another strap can be pulled, with the free ends of both straps being sewn together.

After applying the band about the desired site of the gastrointestinal tract, for example, the stomach inlet, fluid is introduced into the hollow volume of the band to generate the desired constriction, whereby the annular opening encompassed by the band becomes constricted. In addition to stomach bands, devices of this type are also applied in particular as anal bands to close off, if occasion arises, an artificial anus.

SUMMARY OF THE INVENTION

The invention addresses the problem of proposing an improved device of the above described type, and, this is accomplished according to the invention through a device with the characteristics described below.

The invention is based on the fundamental idea of proposing additional safety for the patient by utilizing a safety closure, which opens at a tear-off tension when a predetermined limit value is exceeded. Due to the use of such a safety closure, the band can open in the event that too high a pressure loading is exerted onto it before the body tissue exposed to the pressure loading can be damaged. High pressure loadings can be caused, for example, in the case of stomach bands, by the patient vomiting. Due to the nondestructive opening of the band, it can subsequently be closed again in a relatively simple surgical step without a replacement of the device being required which would be surgically considerably more demanding.

The functional operation of the safety closure and the limit value of the tear-off tension can herein advantageously be independent of the state of filling of the band.

In an advantageous embodiment of the invention, the closure device developed as a safety closure is formed by a cross piece comprising a circumferentially closed opening, which is secured on an end region of the band, and an extension on the other band end, insertable through the opening in the cross piece. The extension is provided with a collar or projection for extending behind the margin of the opening in the cross piece. By employing pairings of material having suitable elasticities for the cross piece and the collar or the projection, as well as a corresponding development of the geometry, for example, the thickness of the cross piece, the desired limit value of the tear-off tension can be attained above which the closure device opens. The thickness of the cross piece can reasonably be less than 5 mm, and preferably less than 4 mm.

In an advantageous embodiment of the invention, furthermore, a connection tubule, separate from the extension, with an inner channel can be provided, which extends from the band in a region between its two ends and whose channel is connected with the hollow volume of the band. Thereby, the application of the band about the body organ, for example, the stomach, is facilitated, and also a possibly later required surgical revision/check as will be explained in further detail in the description of the Figures.

BRIEF DESCRIPTION OF THE DRAWINGS

In the following further advantages and details of the invention will be described in conjunction with the embodiment examples depicted in the attached drawings, which also show further tasks of the invention. In the drawings:

FIG. 1 illustrates a side view of a device according to the invention (in the direction B in FIG. 2);

FIG. 2 illustrates a view (in the direction A in FIG. 1);

FIG. 3 illustrates an end elevational view of the cross piece with the insertion opening without the extension inserted (in the direction C in FIG. 1);

FIG. 4 illustrates a section view along line AA of FIG. 3;

FIGS. 5 to 7 illustrate perspective representations of the device from different angles with the closure part, comprising the cross piece with the insertion opening, depicted in the manner of an exploded view and removed from the band;

FIG. 8 illustrates a schematic representation of a configuration for measuring the tear-off tension;

FIG. 9 illustrates a side view of a further embodiment example of a device according to the invention;

FIG. 10 illustrates a different view of the device of FIG. 10;

FIG. 11 illustrates a top view of the device of FIG. 10;

FIG. 12 illustrates a perspective representation of the device of FIG. 10;

FIG. 13 illustrates a further perspective representation from a different angle of the device of FIG. 10;

FIG. 14 illustrates a section along line DD of FIG. 10;

The Figures are drawn to different scales. Equivalent, or at least analogously acting, parts are provided in both embodiment examples with identical reference symbols.

DETAILED DESCRIPTION OF THE INVENTION

Figure 17:
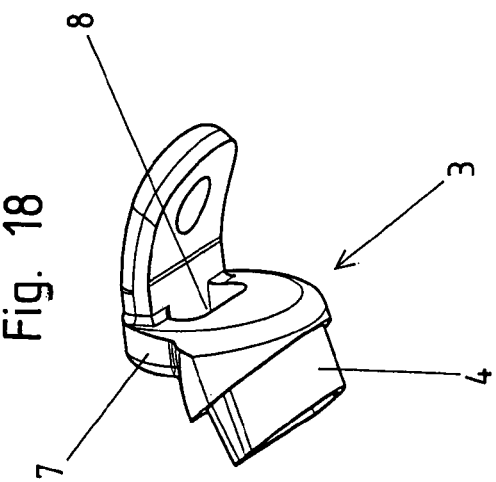
FIGS. 17–18 illustrate the closure part before before its attachment to the main part in perspective representations from different angles.
Figure 18:
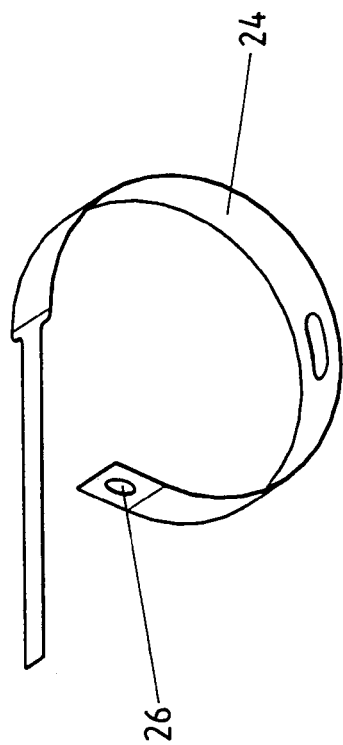

The device developed in the first depicted embodiment example (FIG. 1 to 8) in the form of a stomach band comprises a band 1, comprised, for example, of silicon, to be placed annularly about the corresponding portion of the gastrointestinal tract, here, the stomach, the stomach inlet or the esophagus, which includes a fillable hollow volume 2 extending in its longitudinal direction. The hollow volume 2 extends continuously over the entire length of the tubular band 1. The end regions of the band to be connected with one another when the band is placed annularly about the body organ, are provided with a closure device.

The device according to the invention in this embodiment example is developed in two parts, with a main part 16 and a closure part 3 adhered to the main part 16. The main part 16 comprises the tubular band 1 to be placed annularly about the body organ and an extension 10 disposed on the one end of the band 1. The extension 10 is developed in the form of a tubule and includes an inner channel, which is connected with the hollow volume 2 of band 1.

When the two end regions of band 1 are connected with one another via the closure device 3, which will be explained in further detail, the band 1, which is now annular, encompasses an annular opening 6.

At the other end of the band 1, the closure part 3 is adhered, which also at the end closes off the hollow volume 2 in band 1. The closure part 3 comprises an insertion plug 4 projecting into the end region of the hollow volume 2 of band 1, and a contact plate 5 in contact on the end-side front face of the band. The contact plate 5 also forms an end-side front face of the device, and the insertion plug 4 and the contact plate 5 are adhered to the band 1.

From the side of the contact plate 5 facing away from the annular opening 6 of band 1 projects a cross piece 7 outwardly, whose thickness d is favorably smaller than 5 mm, preferably smaller than 4 mm, and in which an insertion opening 8 is developed. This insertion opening 8 is here formed by a slot-form cutout with a widened central region extending upwardly and downwardly. As is evident in FIG. 4, an edge 9 of the insertion opening 8 is, at least in some regions, beveled, and the insertion opening widens toward the side disposed above in FIG. 4 (this is the insertion side for the extension 10, as will be evident more extensively in the following). In the embodiment example shown, those sections of edge 9 are provided with beveling which in FIG. 3 form the left and the right boundary of the insertion opening 8 as well as the entire lower boundary. Only the section forming the upper boundary does not comprise such a beveling. At the end, facing away from the annular opening 6 of cross the piece 7 is further disposed a tension tab 15, which facilitates retention of the cross piece when closing the device developed here as a stomach band.

Onto the free end of the extension 10, an end of a tubing can be placed, via which the hollow volume 2 of band 1 can be filled with fluid in order to decrease the cross section of the annular opening 6 correspondingly, wherein the inner boundary wall, facing the annular opening 6, of the tubular band expands inwardly. The outer boundary wall is herein advantageously provided with a high tensile-strength reinforcement layer to restrict or prevent the expansion of the outer boundary wall. The fluid can be introduced, for example, in a conventional manner, by means of an injection port or by means of a pumping device.

On the extension 10 is disposed a projection 11 which, in the embodiment example shown, projects on all sides beyond the extension 10. The width of the projection 11 is herein the least on the side of the extension facing the annular opening 6. The projection 11 has the greatest width in portions of its section which extends beyond the side of the extension 10 facing away from the annular opening 6.

In the direction toward the free end of the extension 10, the projection 11 comprises a form extending from the extension 10 and conically widening, in order to make possible the pulling-through through the insertion opening 8. On the opposing side, which extends behind the edge of the insertion opening 8 when it is inserted, the projection 11 is developed in the form of steps and projects approximately perpendicular from the extension 10.

On the tubular extension 10 are additionally disposed four ribs 12 each spaced apart from the other by 90 degrees in the circumferential direction, extending in the longitudinal direction of extension 10 and projecting outward. The ribs 12 counteract the kinking of the extension 10 and the closing of its opening entailed therein.

For developing a safety closure, the closure device of the device according to the invention opens upon a tear-off tension which exceeds a limit value, and this limit value is in the range of between 20 and 60 N. Especially preferred is a range between 30 and 50 N. The tear-off tension is herein measured in a manner as shown schematically in FIG. 8. The closed device is placed around cams 13, 14 of which at least one is developed to be movable. The distance of the two cams is increased until the closure device opens. One half of the value of the force required for this purpose represents the tear-off tension of the closure device.

Due to the depicted and described development of the closure device formed of an elastic material, preferably of silicon, the closure device can open free of destruction at a value above the predetermined limit value of the tear-off tension and also can be subsequently closed again. Due to the least width of projection 11 on the side facing the annular opening 6, pulling the projection 11 through the insertion opening 8 upon the effect of a tear-off tension starts in this region. Due to the greatest width of projection 11 on the side facing away from the annular opening 6, the projection 11 is initially retained here. The lateral regions of the projection 11, which project beyond the sides of the extension 10, which are oriented in the direction of the narrow sides of the band 1, start to curl increasingly and are more and more pulled through the insertion opening 8, until the section of projection 11, removed from the annular opening 6, is also pulled through the opening 8. This process is also assisted through the beveled sections of the edge 9 of the insertion opening 8.

As the material for the cross piece 7 and the projection 11, for example, silicon with a hardness in the region of 70 Shore A (±5 Shore A) can be used.

A further embodiment example of the invention is depicted in FIGS. 9 to 18, and the device is again developed as a stomach band. The device again comprises a band 1 provided with a continuous hollow volume 2, whose one end is closed by an adhered closure part 3 and at whose other end an extension 10 is disposed. The closure part 3 and the extension 10 are provided with cooperating parts of a closure device, in the closed state of which the tubular band 1 is closed annularly and encompasses an annular opening 6.

The closure device again comprises a cross piece 7 projecting outward, in which a circumferentially closed insertion opening 8 is developed, but whose margins here do not extend parallel, as well as a projection 11 disposed on the extension 10. To close the device, the extension 10 is pulled through the insertion opening 8, until the projection 11 has been pulled through the insertion opening 8 (with the elastic widening of the same) and on the side opposing the introduction side of a cross piece 7 extends beyond the edges of the insertion opening 8. In this case, the projection 11 only projects beyond the extension 10 on the side facing away from the annular opening 6 of the extension 10 and on the two sides of the extension 10 oriented in the direction of the narrow sides of the band 1. On the inside of extension 10, thus in the direction toward the annular opening 6, the extension 10 is, in contrast, developed smoothly in this region.

To facilitate the closing of the band 1, the extension 10 is provided with a pull strap 17, and specifically in a segment located in the direction, viewed from the projection 11, toward the free end of the extension 10. The pull strap 17 comprises a snap hook 18.

In this embodiment example, the extension 10 is not provided with a channel penetrating the extension 10, but rather a connection tubule 19 separate from the extension 10 is provided, which has an inner channel 20 connected with the hollow volume 2 of the band 1. The connection tubule extends from the band 1 in the region between its two ends, with a longitudinal axis 21 of the connection tubule forming with a circumferential line 22 of the band 1 an angle 23 of less than 60 degrees, and preferably less than 45 degrees. The connection tubule 19, consequently, projects more or less tangentially from the band 1.

The device furthermore comprises a reinforcement layer 24, which extends continuously through the outer wall of the band 1 over the entire length of the band 1 and through the extension 10, preferably up to its free end.

This reinforcement layer 24 comprises filaments continuous in the longitudinal direction and advantageously also in the transverse direction over its entire extent and can be developed in particular as a woven rectangle fabric of, for example, a synthetic material. This reinforcement layer reinforces, on the one hand, the outer wall of the band 1, to prevent an expansion of the outer wall during the filling of the band 1, and, on the other hand, the connection between the band 1 the and the extension 10, as well as protecting, furthermore, the pull strap 17 against the tensile stress, as is exerted during the application of the device and during its closure.

The band 1 comprises advantageously a softer material than the end the piece 3 and extension 10 with the components of the closure device disposed thereon. For the example, the band 1 can have a hardness in the range of 20 to 40 Shore A and the parts of the closure device a hardness in the region of 70 Shore A. All parts of the device with the exception of the reinforcement layer can be comprised of silicon.

The extension 10 continues in the proximity of the outer wall of the band 1 beyond the end of the band 1. An end-side front wall 25 closing the hollow volume 2 of the band 1 on the side of the extension 10, thus projects inward with respect to the extension 10 and this front wall is also comprised of the soft material of the band 1.

Figure 16:
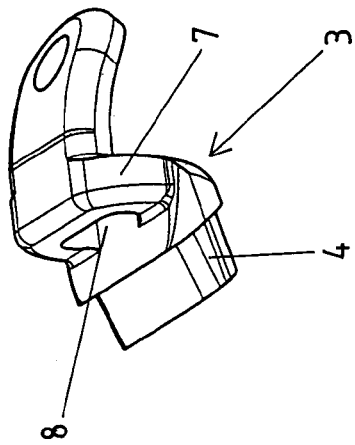
FIG. 16 illustrates the main part of the device after the injection molding process.
Figure 15:
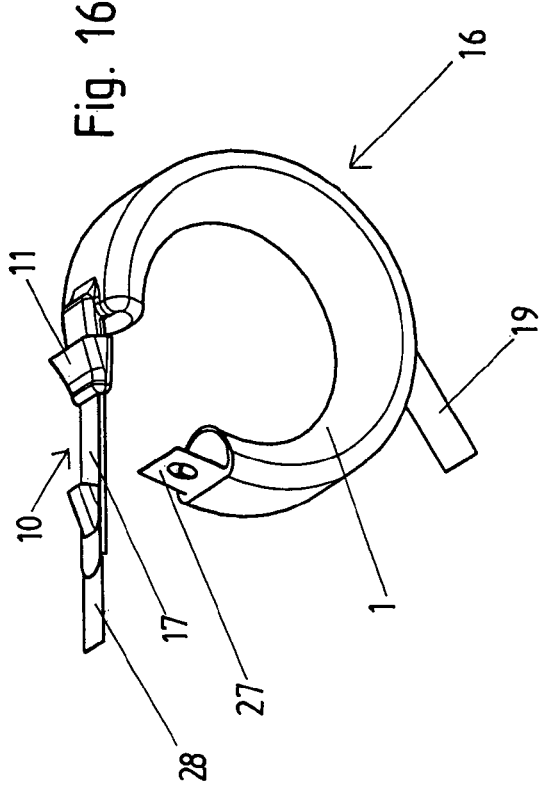
FIG. 15 illustrates a reinforcement layer utilized in the production of the device.

For the manufacture of the band, the reinforcement layer 24 depicted in FIG. 15 is suspended with an opening 26 in a core disposed in the hollow volume 2. After the synthetic material has been injected into the hollow mold volume and the core has been pulled out of the hollow volume 2 of the band 1, the main part shown in FIG. 16 is obtained, and the segments 27, 28, projecting beyond the pull strap 17 and the end of the band 1, of the reinforcement layer 24 are cut off. Subsequently, the closure part 3 depicted in FIGS. 17 and 18 with its insertion plug 4 is slid into the hollow volume 2 at the ends of the band 1 opposing the extension 10 and adhered with the band 1.

After the appropriate preparation of the surgical site, to apply the stomach band about the stomach, the band 1 is pulled around the stomach, with surgical forceps grasping the pull strap 17. The tubule 19 does not need to be pulled around the stomach and also during the operation, no tensile stress of this tubule 19 takes place, such that it can be developed from a soft, body-friendly material of, for example, the same hardness as the band 1 and preferably also of silicon. When pulling the band 1 about the stomach, the risk of injuries to blood vessels is strongly reduced, since no projecting sharp edges counteract this pulling-around. The snap hook 18 and the projection 11 decrease conically in the direction toward the free end of the extension 10, and the front wall 25 comprises a soft elastic material and thus can readily bend in the direction toward the outer wall of the band 1.

After the band 1 has been pulled around the stomach, the pull strap 17 is introduced into the insertion opening 8 until the snap hook 18 first hooks onto the edge of the insertion opening 8. Subsequently, surgical forceps grasps the pull strap 17 as well as the tension tab 15 and the projection 11 is pulled through the insertion opening 8, such that the closure device is snapped in. As described in connection with the first embodiment example, the closure device is developed as a safety closure self-opening above a predetermined limit value of a tear-off tension.

It may occur that a subsequent surgical revision/check, i.e., a new placement of the band 1 is required, for example, if the band has slipped or if a stomach expansion has formed in another region, to which the band is to be transposed. The closure device developed as a safety closure of the stomach band can herein be opened by applying a corresponding traction, without destruction, and the band 1 can be removed from the stomach and at the new site again be placed about the stomach and closed. Since the tubule 19 is disposed separate from the closure device on the band 1, the tubule 19 can herein remain connected with the injection port, such that a second surgical site at the injection port can be avoided. The tubule 19, which is only depicted in the Figures as a short tube piece, can be developed to be significantly longer and extend continuously to the injection port, such that the application of an intermediate piece (with the potential of leakage or detachment of the connection) can be omitted.

Different modifications of the depicted embodiment examples of the invention are conceivable and possible without leaving the scope of the invention. Depending on the material employed, the thickness d of cross piece 7, which in the depicted embodiment examples is approximately 3 mm, or the width of the projection on the different sides of the extension can, for example, be varied.

A device according to the invention could furthermore not only be applied as a stomach band, but, for example, also for closing an artificial or natural outlet of intestines, and for closing and opening the intestine outlet, fluid can be introduced into the band or drained from it by means of a (conventional) reservoir with variable volume.

LEGEND OF REFERENCE SYMBOLS

1 Band
2 Hollow volume
3 Closure part
4 Insertion plug
5 Contact plate
6 Annular opening
7 Cross piece
8 Insertion opening
9 Edge
10 Extension
11 Projection
12 Rib
13 Cam 14 Cam
15 Tension tab
16 Main part
17 Pull strap
19 Connection tubule
20 Channel
21 Longitudinal axis
22 Circumferential line
23 Angle
24 Reinforcement layer
25 Front wall
26 Opening
27 Segment
28 Segment

The invention claimed is:

1. A device for generating an artificial constriction in a gastrointestinal tract, the device comprising:
   a band adapted to be placed annularly about a particular portion of the gastrointestinal tract, said band comprising a fillable hollow volume and a pair of end regions; and
   a safety closure device for connecting said end regions of said band placed annularly about the portion of the gastrointestinal tract, said safety closure device being operable to automatically open without destruction at a tear-off tension exceeding a limit value and operable to be closed again after opening,
   wherein the limit value of the tear-off tension is in a range between 20 and 60 N, and
   wherein said safety closure device comprises a cross piece having a circumferentially closed insertion opening, said cross piece being secured on a first of said end regions of said band, an extension insertable through the circumferentially closed insertion opening on said cross piece, said extension extending from a second of said end regions of said band and having a projection extending on a side of the cross piece facing away from said second end region when said safety closure device is closed, and a pull strap provided with said extension, said pull strap extending further way from said cross piece than said projection.

2. A device as claimed in claim 1, wherein the limit value of the tear-off tension is in the range between 30 and 50 N.

3. A device as claimed in claim 1, further comprising a closure part adhered to said first end region of said band, said closure part closing the fillable hollow volume of said band at said first end region, wherein said cross piece is disposed on said closure part.

4. A device as claimed in claim 1, wherein said cross piece and said projection are comprised of silicon with a hardness in the region of 70 Shore A.

5. A device as claimed in claim 1, wherein said projection projects at least beyond a side of said extension facing away from an annular opening formed by the device and two sides of said extension opposite to each other and adjoining said side of said extension facing away from the annular opening.

6. A device as claimed in claim 5, wherein a width of said projection in proximity to a side of said extension facing the annular opening is narrower than a width of said projection in proximity to remaining sides of said extension or said side of said extension facing the annular opening and in proximity to said projection is substantially smooth.

7. A device as claimed in claim 5, wherein a width of said projection in proximity to said side of said extension facing away from the annular opening is at least partially wider than a width of said projection in proximity to said two sides of said extension opposite to each other and adjoining said side of said extension facing away from the annular opening.

8. A device as claimed in claim 1, wherein said extension has a free end and said projection widens conically in a direction away from said free end of said extension.

9. A device as claimed in claim 1, wherein at least some areas of the circumferentially closed insertion opening are beveled and the circumferentially closed insertion opening widens toward an insertion side of the circumferentially closed insertion opening for said extension.

10. A device as claimed in claim 1, wherein a thickness of said cross piece is less than 5 mm.

11. A device as claimed in claim 10, wherein the thickness of said cross piece is less than 4 mm.

12. A device as claimed in claim 1, further comprising a connection tubule separate from said extension, said connection tubule having an inner channel and extending from said band at a region between said first and second end regions of said band, wherein the inner channel is connected with the fillable hollow volume of said band.

13. A device as claimed in claim 12, wherein a longitudinal axis of said connection tubule forms an angle with a circumferential line of said band of less than 60 degrees.

14. A device as claimed in claim 12, wherein said connection tubule is disposed closer to said first end region than said second end region.

15. A device as claimed in claim 1, wherein said pull strap comprises a snap hook.

16. A device as claimed in claim 1, further comprising a continuous high tension-strength reinforcement layer extending over at least a portion of an outer wall of said band and said extension.

17. A device as claimed in claim 16, wherein said reinforcement layer comprises filaments continuous at least in a longitudinal direction.

18. A device as claimed in claim 1, further comprising an end-side front wall for closing the fillable hollow volume of said band at said second end region, said end-side front wall having a hardness in a range of 20 to 40 Shore A.

* * * * *